United States Patent [19]

Szczepanski et al.

[11] 4,311,514
[45] Jan. 19, 1982

[54] SULFUR-CONTAINING ALKANECARBOXYLIC ACID DERIVATIVES WITH HERBICIDAL AND PLANT GROWTH-REGULATING ACTION, PRODUCTION THEREOF AND METHOD OF USE

[75] Inventors: Henry Szczepanski, Rheinfelden; Otto Rohr, Therwil; Hermann Rempfler, Ettingen, all of Switzerland

[73] Assignee: Ciba-Geigy Corporation, Ardsley, N.Y.

[21] Appl. No.: 183,613

[22] Filed: Sep. 2, 1980

[30] Foreign Application Priority Data

Sep. 13, 1979 [CH] Switzerland .................. 8297/79

[51] Int. Cl.$^3$ ................... A01N 43/40; A01N 41/00; A01N 31/04; C07C 149/31
[52] U.S. Cl. ................... 71/94; 260/455 R; 260/465 D; 546/288; 546/297; 546/302; 564/162; 564/166; 564/167; 564/168; 560/9; 560/15; 71/103; 71/98; 71/100
[58] Field of Search ................ 260/455 R, 465 D; 546/288, 297, 302; 564/162, 166, 167, 168; 560/9, 15; 71/94, 103, 98, 100

[56] References Cited

U.S. PATENT DOCUMENTS 4,183,743  1/1980  Rohr et al. .................. 260/455 R

OTHER PUBLICATIONS

Noller, Textbook of Organic Chemistry, 2nd Ed., W.B. Saunders Company, Philadelphia, pp. 211, 102.

Primary Examiner—John M. Ford
Assistant Examiner—Robert C. Whittenbaugh
Attorney, Agent, or Firm—Frederick H. Rabin

[57] ABSTRACT

The sulfur-containing alkanecarboxylic acids of the formula

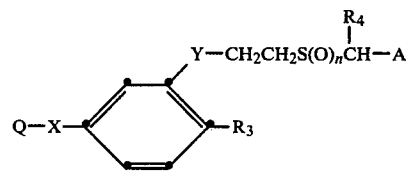

possess herbicidal and plant growth-regulating properties. In this formula, A is the cyano group, the carboxyl group, a carboxylic acid salt or a carboxylic acid ester, thioester, or carboxamide radical, n is 0, 1 or 2, Q is a substituted phenyl or pyrid-2-yl radical, $R_3$ is a halogen atom, cyano, or nitro group, $R_4$ is $C_1$–$C_6$alkyl, $C_2$–$C_6$alkenyl or $C_2$–$C_6$alkynyl, phenyl or benzyl, $C_2$–$C_6$alkoxyalkyl or $C_3$–$C_{12}$cycloalkyl.

14 Claims, No Drawings

SULFUR-CONTAINING ALKANECARBOXYLIC ACID DERIVATIVES WITH HERBICIDAL AND PLANT GROWTH-REGULATING ACTION, PRODUCTION THEREOF AND METHOD OF USE

The present invention relates to novel sulfur-containing alkanecarboxylic acid derivatives, the production thereof, herbicidal and plant growth-regulating compositions containing these novel compounds, and the use thereof.

In addition to numerous variously substituted phenoxy-phenoxyalkanecarboxylic acids and pyridyloxyphenoxyalkanecarboxylic acids and derivatives thereof, corresponding 3-and 4-phenoxyphenoxyalkanols and their corresponding phenylthio analogues, mercaptans, esters and amines, as well as further derivatives, have become known from the literature (cf. German Offenlegungsschrift Nos. 2 611 695 and 2 533 172, and U.S. Pat. Nos. 4 046 798 and 4 093 446).

It has now been found that certain derivatives of 3-phenoxyalkylthiosulfinyl- and -sulfonylalkanecarboxylic acid and of 3-pyridyloxyphenoxyalkylthiosulfinyl- and -sulfonylalkanecarboxylic acid are in many ways superior to these prior art compounds in their herbicidal and plant growth-regulating action.

The compounds of the present invention have the formula I

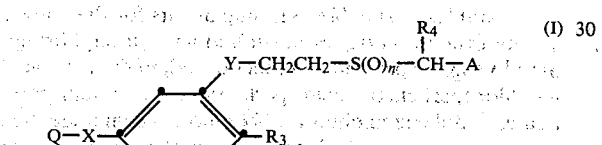

wherein Q is a radical

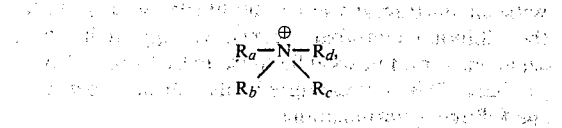

A is the cyano group or a —COB radical, B is a —OR$_5$, —SR$_6$, —NR$_7$R$_8$ radical, R$_1$ is a halogen atom, n is 0, 1 or 2, R$_2$ is a halogen atom, the trifluoromethyl, nitro or cyano group, R$_3$ is a halogen atom or the nitro or cyano group, R$_4$ is C$_1$-C$_6$alkyl, C$_2$-C$_6$alkenyl, C$_2$-C$_6$alkynyl; benzyl or phenyl, each of which may be substituted by halogen; or is C$_2$-C$_6$alkoxyalkyl or C$_3$-C$_{12}$cycloalkyl, R$_5$ is hydrogen or the cation of a base 1/m M$^{m\oplus}$, wherein M is an alkali metal cation or an alkaline earth metal cation, or an iron, copper, zinc, manganese or nickel cation or an ammonio radical $$R_a \overset{\oplus}{\underset{R_b}{\overset{|}{N}}} R_c$$

m as an integer 1, 2 or 3 corresponds to the valency of the cation, whilst each of R$_a$, R$_b$, R$_c$ and R$_d$ independently is hydrogen, benzyl, or a C$_1$-C$_4$alkyl radical which can be substituted by —OH, —NH$_2$ or C$_1$-C$_4$alkoxy; each of R$_5$ and R$_6$ is also a C$_1$-C$_{18}$alkyl radical which is unsubstituted or substituted by halogen, nitro, cyano, C$_1$-C$_8$alkoxy, C$_2$-C$_8$alkoxy-alkoxy, C$_3$-C$_6$alkenyloxy, C$_1$-C$_8$alkylthio, C$_2$-C$_8$alkanoyl, C$_2$-C$_8$acyloxy, C$_2$-C$_8$alkoxycarbonyl, carbamoyl, bis(C$_1$-C$_4$alkyl) amino, tris(C$_1$-C$_4$alkyl)ammonio, C$_3$-C$_8$cycloalkyl, C$_3$-C$_8$cycloalkenyl, or also by a phenoxy or 5- or 6-membered heterocyclic radical containing 1 to 3 hetero-atoms, each of which is unsubstituted or is itself substituted by one or more of halogen, C$_1$-C$_4$alkyl or C$_1$-C$_4$alkoxy; or is a C$_3$-C$_{18}$alkenyl radical which is unsubstituted or mono- to tetrasubstituted by halogen or monosubstituted by phenyl or methoxycarbonyl; a C$_3$-C$_8$alkynyl radical; a C$_3$-C$_{12}$cycloalkyl radical which is unsubstituted or substituted by halogen or C$_1$-C$_4$alkyl; a C$_3$-C$_8$cycloalkylene radical; a phenyl radical which is unsubstituted or substituted by one or more of halogen, C$_1$-C$_4$alkyl, C$_1$-C$_4$alkoxy, C$_1$-C$_4$alkylthio, NO$_2$, CF$_3$, COOH, CN, OH, SO$_3$H, NH$_2$ or —NH(C$_1$-C$_4$alkyl) or —N(C$_1$-C$_4$alkyl)$_2$; a 5- to 6-membered heterocyclic ring containing 1 to 3 hetero atoms; each of R$_7$ and R$_8$ independently is hydrogen, a C$_1$-C$_6$alkyl radical which can be interrupted by oxygen or substituted by halogen, hydroxy or cyano; a C$_2$-C$_6$alkenyl or C$_2$-C$_6$alkynyl radical which can be substituted by halogen; a C$_3$-C$_8$cycloalkyl radical; a phenyl or benzyl radical which can be substituted by halogen, C$_1$-C$_4$alkyl, alkoxy or alkylthio, nitro, cyano or trihalomethyl; or R$_7$ and R$_8$, together with the nitrogen atom to which they are attached, can also form a heterocyclic ring; and each of X and Y is an oxygen or a sulfur atom.

The alkyl radicals in the above formula can be branched or unbranched. R$_7$ and R$_8$ can be hydrogen or aliphatic or aromatic radicals, or, together with the nitrogen atom to which they are attached, they can form a preferably 5 or 6-membered heterocyclic ring system which can additionally contain a second heteroatom. Preferred identities for R$_7$ and R$_8$, however, are hydrogen, lower alkyl and also branched alkenyl and alkynyl e.g. allyl, methallyl, 2,2-dimethylallyl, 2,2-dimethylpropargyl and 2,2-diethylpropargyl.

Especially active compounds are those of the formula I is which Q is a 2,4-dichlorophenyl, 3,5-dichloropyrid-2-yl, 2-chloro-4-trifluoromethylphenyl or 3-chloro-5-trifluoromethylpyrid-2′-yl radical, each of X and Y is oxygen, R$_3$ is a halogen atom, the nitro or cyano group, n is 0, R$_4$ is hydrogen or methyl, and A is a C$_1$-C$_{18}$alkoxycarbonyl or C$_2$-C$_8$alkoxyalkoxycarbonyl group.

The compounds of the formula I possess herbicidal activity in preemergence and postemergence applications and they can be employed as weed-killers in crops of monocots and dicots. In addition, they possess useful growth regulating properties (growth inhibition). In particular, they inhibit the growth of dicots. Exemplary of the useful application of the compounds of the present invention are:

the reduction of the vegetative growth in soybeans and similar leguminous plants, resulting in an increase in the yield of these crops;

the inhibition of the undesirable growth of suckers in tobacco plants, the leading shoots of which have been cut, thus promoting the formation of larger and finer leaves;

the inhibition of the growth of grass and dicotyledonous plants, such as fruit trees, ornamental trees, bushes and hedgerows, with the object of saving cutting work;

the desiccation and defoliation of plants, e.g. potatoes and cotton, shortly before harvesting.

The rate of application is between 0.1 and 5 kg per hectare for achieving the desired herbicidal or growth regulating action.

The novel compounds of the formula I are obtained by methods which are in themselves known, for example in accordance with the following synthesis routes:

A phenol or thiophenol of the formula II

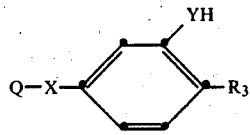

wherein Q, R₃, X and Y are as defined for formula I, is reacted, in a polar organic solvent and in the presence of an acid acceptor, firstly with a dihaloethane of the formula III

wherein Hal is halogen, preferably chlorine or bromine, and then the haloethoxybenzene or haloethylthiobenzene thereby obtained is reacted, in a polar organic solvent and in the presence of an acid acceptor, with a derivative of an α-thio-, α-sulfinyl- or α-sulfonylalkylcarboxylic acid of the formula IV

wherein A, n and R₄ are as defined for formula I.

Another method of obtaining the compounds of formula I consists in reacting a compound of the formula V

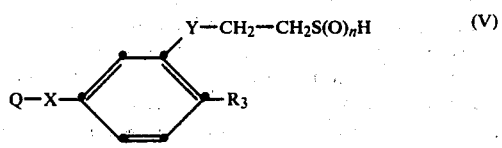

wherein n, Q, R₃, X and Y are as defined for formula I, in a polar organic solvent and in the presence of an acid acceptor, with an α-halocarboxylic acid derivative of the formula VI

wherein Hal is halogen, especially chlorine or bromine, and A and R₄ are as defined for formula I.

The compounds of the formula I are also obtained by reacting a phenol or thiophenol of the formula II, in a polar solvent and in the presence of an acid acceptor, with a haloethylthio-, -sulfinyl- or -sulfonylalkanecarboxylic acid derivative of the formula VII

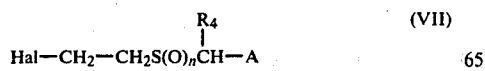

wherein Hal is halogen, especially chlorine or bromine, and A, n and R₄ are as defined for formula I.

Finally, the sulfinyl and sulfonyl compounds of the formula I are also obtained by oxidising a compound of the formula Ia

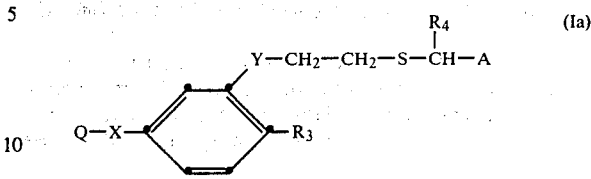

wherein A, Q, R₃, R₄, X and Y are as defined for formula I, in a solvent which is inert to the reactants, with an oxidising agent.

The above reactions are conducted in the presence of solvents or diluents which are inert to the reactants. Preferred solvents are polar organic solvents such as methyl ethyl ketone, dimethyl formamide, dimethyl sulfoxide etc. The reaction temperatures are in the range from 0° to 200° C. and the reaction time is from 1 hour to several days, depending on the starting material, reaction temperature, and solvent. The reaction is usually carried out under normal pressure. Suitable bases (condensation agents) for the above reactions are those normally employed, e.g. KOH, NaOCH₃, NaHCO₃, K₂CO₃, potassium tert-butylate, and also organic bases such as triethylamine.

Examples of suitable oxidising agents for the conversion of the thio bridges to sulfinyl and sulfonyl bridges are hydrogen peroxide, peracetic acid, perbenzoic acid, 4-chloroperbenzoic acid, perlauric acid, sodium periodate, iodobenzodichloride, N-chlorosuccinimide, and N-bromosuccinimide. Depending on the oxidising agent employed, suitable solvents are methylene chloride, chloroform, acetic acid, water etc. Similar oxidation reactions are described e.g. in "Organic Compounds of Bivalent Sulfur", Vol. 2, page 64 (Chemical Publishing Co., New York, 1960).

Some of the starting materials of the formulae II to VII are known. Still undisclosed starting materials of these formulae can be easily prepared by conventional processes. Phenoxyphenols of the formula II can be obtained e.g. by the methods described in J. Am. Chem. Soc. 61, 2702 (1939), or in Chem Abstract 52, 9006b (1958). The production of such phenoxyphenols is also described in German Offenlegungsschrift No. 2 433 066.

The compounds of formula I are of low mammalian toxicity and their handling and application cause no problems.

The compounds of the formula I are stable compounds which are soluble in customary organic solvents such as alcohols, ethers, ketones, dimethyl formamide, dimethyl sulfoxide etc.

The compositions of the present invention are obtained in known manner by intimately mixing and grinding compounds of formula I (active ingredients) with suitable carriers and/or adjuvants, with or without the addition of anti-foam agents, wetting agents, dispersants and/or solvents which are inert to the active ingredients. The active ingredients can be processed to the following formulations:

solid formulations: dust, tracking powders, granules (coated granules, impregnated granules and homogeneous granules), active ingredient concentrates which are dispersible in water:

wettable powders, pastes, emulsions, emulsifiable concentrates:

liquid formulations: solutions, dispersions.

The concentrations of active ingredient in the compositions of this invention are between 1 and 80 percent by weight. As circumstances may require, the active ingredients can also be applied in low concentrations of about 0.05 to 1 percent by weight.

The compositions of the present invention can be mixed with other biocidal compounds.

The following Examples will serve to illustrate the invention in more detail. Pressures are in millibars and parts and percentages are by weight.

EXAMPLE 1

Production of a compound of the formula I

Methyl 3-(2'-chloro-4'-trifluoromethylphenoxy)-6-chloro-phenoxyethylthioacetate 20.7 g of potassium carbonate, 19.2 g (0.05 mole) of 3-(2'-chloro-4'-trifluoromethylphenoxy)-6-chloro-phenoxy-chloroethane and 5.3 g (0.05 mole) of methyl thioglycolate are added at room temperature to 80 ml of dimethyl sulfoxide. In the course of the exothermic reaction, the temperature rises to about 42° C. The reaction mixture is then stirred overnight at room temperature. On the next day, the batch is diluted with 300 ml of ether and the ethereal solution is washed with two 400 ml portions of 20% $K_2CO_3$ solution. The organic phase is dried over magnesium sulfate and concentrated, affording 17.8 g of a light yellow oil with a refractive index of $n_D^{21}$ 1.5487. The following compounds were obtained in analogous manner:

Cl–⟨ ⟩–O–⟨Cl⟩–O–⟨ ⟩–R$_3$ with O–CH$_2$CH$_2$SCH(R$_4$)–COOR$_5$

| R$_3$ | R$_4$ | R$_5$ | Physical data |
|---|---|---|---|
| Cl | H | C$_3$H$_7$iso | $n_D^{22}$ 1.5688 |
| Cl | H | C$_2$H$_5$ | $n_D^{22}$ 1.5778 |
| Cl | H | CH$_3$ | $n_D^{25}$ 1.5813 |
| Cl | H | C$_2$H$_4$OCH$_3$ | $n_D^{23}$ 1.5644 |
| Cl | H | C$_4$H$_9$n | $n_D^{23}$ 1.5582 |
| Cl | H | C$_8$H$_{17}$i | $n_D^{23}$ 1.5450 |
| Cl | CH$_3$ | C$_2$H$_5$ | $n_D^{22}$ 1.5529 |
| Br | CH$_3$ | CH$_3$ | |
| Br | CH$_3$ | C$_3$H$_7$iso | |
| CN | CH$_3$ | CH$_3$ | |
| CN | CH$_3$ | CH$_3$ | |
| CN | H | CH$_3$ | |

CF$_3$–⟨ ⟩–⟨Cl⟩–O–⟨ ⟩–R$_3$ with OCH$_2$CH$_2$SCH(R$_4$)–COOR$_5$

| R$_3$ | R$_4$ | R$_5$ | Physical data |
|---|---|---|---|
| Cl | CH$_3$ | CH$_3$ | $n_D^{22}$ 1.5430 |
| Cl | H | C$_2$H$_5$ | $n_D^{22}$ 1.5458 |
| Cl | CH$_3$ | C$_2$H$_5$ | $n_D^{22}$ 1.5381 |
| Cl | H | CH$_3$ | $n_D^{22}$ 1.5487 |
| Cl | H | C$_4$H$_9$n | $n_D^{22}$ 1.5325 |

-continued

CF$_3$–⟨ ⟩–⟨Cl⟩–O–⟨ ⟩–R$_3$ with OCH$_2$CH$_2$SCH(R$_4$)–COOR$_5$

| R$_3$ | R$_4$ | R$_5$ | Physical data |
|---|---|---|---|
| Cl | H | C$_8$H$_{17}$iso | $n_D^{23}$ 1.5189 |
| Cl | H | C$_2$H$_4$OCH$_3$ | $n_D^{21}$ 1.5351 |
| NO$_2$ | CH$_3$ | CH$_3$ | $n_D^{23}$ 1.5435 |
| NO$_2$ | H | C$_4$H$_9$n | $n_D^{22}$ 1.5378 |
| NO$_2$ | H | C$_2$H$_5$ | $n_D^{22}$ 1.5460 |
| NO$_2$ | CH$_3$ | C$_2$H$_5$ | $n_D^{23}$ 1.5340 |
| NO$_2$ | H | C$_3$H$_7$iso | $n_D^{27}$ 1.5621 |
| NO$_2$ | H | C$_2$H$_4$OCH$_3$ | $n_D^{27}$ 1.5430 |

CF$_3$–⟨N⟩–⟨Cl⟩–O–⟨ ⟩–R$_3$ with OCH$_2$CH$_2$SCHCOOR$_5$ (R$_4$)

| R$_3$ | R$_4$ | R$_5$ | Physical data |
|---|---|---|---|
| Cl | CH$_3$ | CH$_3$ | |
| Cl | H | CH$_3$ | |
| CN | CH$_3$ | CH$_3$ | |
| CN | H | C$_2$H$_5$ | |
| NO$_2$ | CH$_3$ | CH$_3$ | |
| NO$_2$ | H | CH$_3$ | |

Cl–⟨N⟩–⟨Cl⟩–O–⟨ ⟩–R$_3$ with OCH$_2$CH$_2$SCHCOOR$_5$ (R$_4$)

| R$_3$ | R$_4$ | R$_5$ | Physical data |
|---|---|---|---|
| Cl | CH$_3$ | CH$_3$ | $n_D^{30}$ 1.5790 |
| Cl | H | CH$_3$ | $N_D^{30}$ 1.5988 |
| NO$_2$ | CH$_3$ | CH$_3$ | |
| NO$_2$ | H | CH$_3$ | |
| CN | CH$_3$ | CH$_3$ | |
| CN | H | CH$_3$ | |

EXAMPLE 2

Production of a number of solid and liquid formulations

Granules

The following substances are used to formulate 5% granules:

5 parts of methyl 3-(2',4'-dichlorophenoxy)-6-chloro-phenoxyalkylthioacetate,
0.25 parts of epoxidised vegetable oil
0.25 parts of cetyl polyglycol ether,
3.50 parts of polyethylene glycol,
91 parts of kaolin (particle size 0.3–0.8 mm).

The active ingredient is mixed with the epoxidised vegetable oil and dissolved in 6 parts of acetone, and the polyethylene glycol and cetyl polyglycol ether are then added. The resultant solution is sprayed on kaolin and subsequently evaporated in vacuo.

Wettable Powder

The following constituents are used to formulate (a) a 70% and (b) a 10% wettable powder:

(a)
- 70 parts of methyl 3-(4'-trifluoromethylphenoxy)-6-chlorophenoxyethylthioacetate,
- 5 parts of sodium dibutylnaphthylsulfonate,
- 3 parts of naphthalenesulfonic acid/phenolsulfonic acid/formaldehyde condensate (3:2:1),
- 10 parts of kaolin,
- 12 parts of Champagne chalk;

(b)
- 10 parts of the above compound,
- 3 parts of a mixture of the sodium salts of saturated fatty alcohol sulfates,
- 5 parts of naphthalenesulfonic acid/formaldehyde condensate,
- 83 parts of kaolin.

The respective active ingredient is applied to the corresponding carriers (kaolin and chalk) and then these are mixed and ground, to yield wettable powders of excellent wettability and suspension powder. By diluting these wettable powders with water it is possible to obtain suspensions containing 0.1 to 80% of active ingredient. These suspensions are suitable for controlling weeds in cultivations of plants.

Paste

The following substances are used to formulate a 45% paste:
- 45 parts of methyl 3-(4'-trifluoromethylphenoxy)-6-chlorophenoxyethylthioacetate or another compound of formula I,
- 5 parts of sodium aluminium silicate,
- 14 parts of cetyl polyglycol ether with 8 moles of ethylene oxide,
- 1 part of oleyl polyglycol ether with 5 moles of ethylene oxide,
- 2 parts of spindle oil,
- 10 parts of polyethylene glycol,
- 23 parts of water.

The active ingredient is intimately mixed with the additives in appropriate devices and ground. By diluting the resultant paste with water, it is possible to prepare suspensions of the desired concentration.

Emulsifiable Concentrate

The following ingredients are mixed to formulate a 25% emulsion concentrate:
- 25 parts of methyl 2-[3-(3',5'-dichloropyridyl-2'-oxy)-6-phenoxy]-ethylthioacetate,
- 5 parts of a mixture of nonylphenolpolyoxyethylene and calcium dodecylbenzenesulfonate,
- 15 parts of cyclohexanone,
- 55 parts of xylene.

This concentrate can be diluted with water to give emulsions in suitable concentrations of e.g. 0.1 to 10%.

EXAMPLE 3

The following text methods are employed to establish the biological activity of the compounds of the formula I.

Preemergence herbicidal action (inhibition of germination)

In the greenhouse, immediately after sowing the test plants in seed dishes, the surface of the soil is treated with an aqueous dispersion of the active ingredients, obtained from a 25% emulsifiable concentrate or from a 25% wettable powder with active ingredients which, on account of their insufficient solubility, cannot be formulated to an emulsifiable concentrate. Four different concentration series are used, corresponding to 4, 2, 1 and 0.5 kg of active ingredient per hectare. The seed dishes are kept in the greenhouse at 22°-25° C. and 50-70% relative humidity, and the test is evaluated after 3 weeks.

The following test plants are used:

| | |
|---|---|
| hordeum (barley) | setaria italica |
| triticum (wheat) | echinochloa crus galli |
| zea (maize) | beta vulgaris |
| sorghum hybritun (millet) | sida spinosa |
| oryza (rice) | sesbania exaltata |
| glycine (soya) | amaranthus retroflexus |
| gossypium (cotton) | sinapis alba |
| avena fatua | ipomoea purpurea |
| lolium perenne | gallium aparine |
| alopecurus myosuroides | pastinaca sativa |
| bromus tectorum | rumex sp. |
| cyperus esculentus | chrysanthemum leucum |
| rottboellia exaltata | abultilon sp. |
| digitaria sanguinlis | solanum nigrum |

Postemergence herbicidal action (Contact herbicide)

A large number (at least 7) of weeds and cultivated plants, both monocots and dicots, are sprayed postemergence, in the 4- to 6-leaf stage, with an aqueous active ingredient emulsion in concentrations of 0.06, 0.125, 0.25, 0.5, 1, 2 and 4 kg of active ingredient per hectare, and kept at 24°-26° C. and 45-60% relative humidity. The test is evaluated 15 days after treatment.

Inhibition of vegetative growth in soybean plants

In a field of soybean plants, parcels each measuring 30 by 8 feet were sprayed with aqueous solutions of the active ingredients at a time when the plants were in the 9-10 leaf stage. Untreated parcels were used as controls. At harvest time, 3½ months after application, the average growth in height of the plants in each parcel as well as the yields were determined and compared with those of the untreated control parcels.

Defoliation and desiccation in cotton

In a cotton field, parcels each consisting of 2 rows 20 feet long were sprayed 2 weeks before harvesting with aqueous preparations of the active ingredients. Untreated parcels acted as controls. Defoliation and desiccation in the different parcels were determined on the 3rd, 7th and 14th day after application, and compared with the state of the control plants.

All the compounds specified above were active in these tests. The best results were obtained with the following compounds:

methyl 2-[3-(2'-chloro-4'-trifluoromethylphenoxy)-6-chlorophenoxyethylthio]propionate methyl 3-(2'-chloro-4'-trifluoromethylphenoxy)-6-chlorophenoxyethylthioacetate methyl 3-(2'-chloro-4'-trifluoromethylphenoxy)-6-nitrophenoxyethylthioacetate methyl 2-[3-(2'-chloro-4'-trifluoromethylphenoxy)-6-nitrophenoxyethylthio]propionate ethyl 2-[3-(2'-chloro-4'-trifluoromethylphenoxy)-6-nitrophenoxyethylthio]propionate.

What is claimed is:

1. A compound of the formula

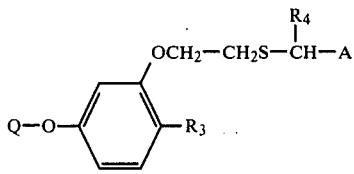

wherein

Q is 2,4-dichlorophenyl, 3,5-dichloropyrid-2-yl, 2-chloro-4-trifluoromethylphenyl or 3-chloro-5-trifluoromethylpyrid-2-yl, $R_3$ is halogen, nitro or cyano, $R_4$ is hydrogen or methyl, and A is a $C_1-C_{18}$ alkoxycarbonyl or a $C_2-C_8$ alkoxyalkoxycarbonyl group.

2. A compound according to claim 1 of the formula

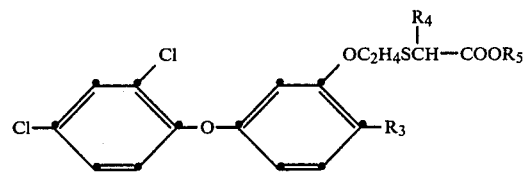

wherein $R_5$ is $C_1-C_{18}$alkyl or $C_2-C_8$alkoxyalkyl.

3. A compound according to claim 1 of the formula

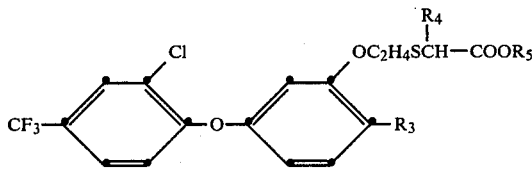

wherein $R_5$ is $C_1-C_{18}$alkyl or $C_2-C_8$alkoxyalkyl.

4. A compound according to claim 1 of the formula

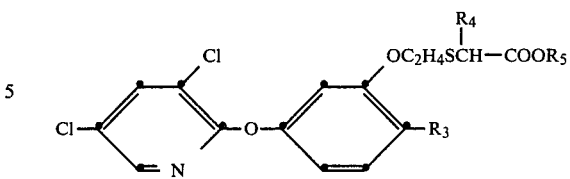

wherein $R_5$ is $C_1-C_{18}$alkyl or $C_2-C_8$alkoxyalkyl.

5. A compound according to claim 1 of the formula

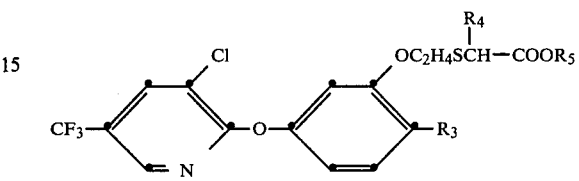

wherein $R_5$ is $C_1-C_{18}$alkyl or $C_2-C_8$alkoxyalkyl.

6. Methyl 3-[3-(2'-chloro-4'-trifluoromethylphenoxy)-6-chlorophenoxyethylthio]propionate according to claim 3.

7. Methyl 3-(2'-chloro-4'-trifluoromethylphenoxy)-6-chlorophenoxyethylthioacetate according to claim 3.

8. Methyl 3-(2'-chloro-4'-trifluoromethylphenoxy)-6-nitrophenoxyethylthioacetate according to claim 3.

9. Methyl 2-[3-(2'-chloro-4'-trifluoromethylphenoxy)-6-nitrophenoxyethylthio]propionate according to claim 3.

10. Ethyl 2[3-(2'-chloro-4'-trifluoromethylphenoxy)-6-nitrophenoxyethylthio]propionate according to claim 3.

11. A herbicidal and plant growth-regulating composition which contains (1) as active component a herbicidally or plant growth-regulating effective amount of a compound according to claim 1, and (2) an inert carrier.

12. A method of controlling weeds at a locus which comprises applying to said locus a herbicidally effective amount of a compound according to claim 1.

13. A method of inhibiting plant growth which comprises applying to plants an effective amount of a compound according to claim 2.

14. A method of desiccating and defoliating cultivated plants shortly before harvesting which comprises applying to said plants an effective amount of a compound according to claim 1.

* * * * *